United States Patent
Katori et al.

(10) Patent No.: US 11,529,293 B2
(45) Date of Patent: Dec. 20, 2022

(54) OIL-IN-WATER EMULSION COSMETIC

(71) Applicant: SHISEIDO COMPANY, LTD., Tokyo (JP)

(72) Inventors: Takahiro Katori, Yokohama (JP); Takashi Matsui, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 278 days.

(21) Appl. No.: 16/463,869

(22) PCT Filed: Dec. 6, 2016

(86) PCT No.: PCT/JP2016/086267
§ 371 (c)(1),
(2) Date: May 24, 2019

(87) PCT Pub. No.: WO2018/105040
PCT Pub. Date: Jun. 14, 2018

(65) Prior Publication Data
US 2019/0290559 A1  Sep. 26, 2019

(51) Int. Cl.
| | |
|---|---|
| *A61K 8/06* | (2006.01) |
| *A61K 8/27* | (2006.01) |
| *A61K 8/29* | (2006.01) |
| *A61K 8/34* | (2006.01) |
| *A61K 8/73* | (2006.01) |
| *A61K 8/86* | (2006.01) |
| *A61Q 17/04* | (2006.01) |
| *A61Q 19/00* | (2006.01) |

(52) U.S. Cl.
CPC ............... *A61K 8/062* (2013.01); *A61K 8/06* (2013.01); *A61K 8/27* (2013.01); *A61K 8/29* (2013.01); *A61K 8/34* (2013.01); *A61K 8/73* (2013.01); *A61K 8/86* (2013.01); *A61Q 17/04* (2013.01); *A61Q 19/00* (2013.01); *A61K 2800/412* (2013.01)

(58) Field of Classification Search
None
See application file for complete search history.

(56) References Cited

U.S. PATENT DOCUMENTS

| | | | | |
|---|---|---|---|---|
| 2007/0014823 | A1* | 1/2007 | Iwata | A61K 8/891 424/401 |
| 2010/0311836 | A1* | 12/2010 | Yamamoto | A61K 8/68 514/561 |
| 2011/0097288 | A1* | 4/2011 | Janssen | A61K 8/375 424/59 |
| 2011/0110989 | A1* | 5/2011 | Simonnet | A61K 8/8152 514/159 |

FOREIGN PATENT DOCUMENTS

| | | |
|---|---|---|
| JP | 2007-84475 | 4/2007 |
| JP | 2012-140334 | 7/2012 |
| JP | 2015-182994 | 10/2015 |
| JP | 5913411 | 4/2016 |
| JP | 2016-74660 | 5/2016 |
| JP | 2015-120682 | 1/2017 |
| WO | WO 2011/065439 | 6/2011 |

OTHER PUBLICATIONS

PCT/JP2016/086267, International Search Report (ISR) and Written Opinion (WO), dated Feb. 7, 2017, 4 pages—English, 15 pages—Japanese.

* cited by examiner

*Primary Examiner* — David J Blanchard
*Assistant Examiner* — Sarah J Chickos
(74) *Attorney, Agent, or Firm* — Andrew F. Young; Nolte Lackenbach Siegel

(57) ABSTRACT

A purpose of the present invention is to provide an oil-in-water emulsion cosmetic having a fresh feeling in use like that of a skin-care cosmetic such as a milky lotion, while also allowing titanium oxide or zinc oxide, which are ultraviolet scattering agents, to be stably blended into the oil phase, and also providing excellent sunscreen effects. The present invention relates to an oil-in-water emulsion cosmetic characterized by comprising (A) an ultraviolet scattering agent having a hydrophobic surface; (B) a water-soluble alkyl-substituted polysaccharide derivative; (C) a higher alcohol; and (D) a non-ionic surfactant. The emulsion cosmetic of the present invention preferably has a viscosity, measured by a B-type viscometer at 30° C., of 12,000 mPa·s or lower.

3 Claims, No Drawings

OIL-IN-WATER EMULSION COSMETIC

CROSS REFERENCE TO RELATED APPLICATIONS

This application relates to and claims priority as a § 371 national phase, from PCT/JP2016/086267 filed Dec. 6, 2016, the entire contents of which are incorporated herein by reference.

FIGURE SELECTED FOR PUBLICATION

None

TECHNICAL FIELD

The present invention relates to an oil-in-water emulsion cosmetic. More specifically, the present invention relates to an oil-in-water emulsion cosmetic that imparts a fresh feeling in use, as in skin-care cosmetics such as milky lotions, and that also has excellent sunscreen effects.

BACKGROUND ART

Skin-care cosmetics are basically for making the skin clean and sufficiently moisturizing the stratum corneum, but cosmetics in which various functions are further added are being studied. For example, when a sunscreen effect is to be added, it is preferable to appropriately combine and blend ultraviolet absorbing agents and powdered ultraviolet scattering agents in order to effectively shield ultraviolet rays from the UVA range to the UVB range. However, particularly in the case of oil-in-water emulsion cosmetics, most ultraviolet absorbing agents are oil-based (oil-soluble) and surface-hydrophobic ultraviolet scattering agents are also blended into the oil phase. Thus, in order to obtain high ultraviolet protection ability, the amount of the oil component must be increased, as a result of which the sense of freshness (dewiness) could be lost and a sticky feeling in use could be imparted.

Patent Document 1 describes an oil-in-water emulsion cosmetic in which a hydrophobically modified alkyl cellulose is used as the emulsifier and a thickener having low salinity tolerance is blended into the water phase. This cosmetic can contain a large amount of an ultraviolet scattering agent in the oil phase while also suppressing the amount of oil that is blended, and when this cosmetic is applied to the skin with the fingers or the like, it undergoes a sudden viscosity reduction and provides a distinctively fresh feeling in use as if collapsing. However, this cosmetic cannot be considered to be adequate in terms of stably holding the ultraviolet scattering agent in the oil phase.

On the other hand, Patent Document 2 describes an oil-in-water emulsion cosmetic that stably holds hydrophobically treated titanium oxide having an average particle size (diameter) of at least 0.1 µm in the oil phase, due to a higher alcohol and a non-ionic surfactant forming an aggregate (α-gel) comprising a lamellar bimolecular film in the presence of water. This cosmetic is excellent in terms of ultraviolet scattering agent stabilization but is not satisfactory in terms of providing a fresh feeling in use.

In particular, it is known that, in low-viscosity oil-in-water emulsion cosmetics, powders of titanium oxide, zinc oxide and the like, which are ultraviolet scattering agents, tend to precipitate and aggregate over time. Patent Document 3 describes a low-viscosity (500 to 8000 mPa·s) oil-in-water emulsion cosmetic containing an alkyl-modified carboxyvinyl polymer and/or a carboxyvinyl polymer, in which titanium oxide containing substantially no aluminum is employed, the surface thereof is coated with silica and further hydrophobically treated, and this modified titanium oxide is blended into the oil phase. However, it is necessary to use a modified titanium oxide that has been subjected to special treatments as mentioned above, and the production process must be monitored to ensure that aluminum does not become intermixed therein. Thus, there were problems in terms of the production cost and the complexity of the production process.

RELATED ART

Patent Documents

Patent Document 1: JP 2015-120682 A
Patent Document 2: JP 5913411 B
Patent Document 3: JP 2007-84475 A

SUMMARY OF THE INVENTION

Problem to be Solved by the Invention

Thus, a problem addressed by the present invention is to provide an oil-in-water emulsion cosmetic achieving a fresh feeling in use as if a skin-care cosmetic such as a milky lotion does, while also allowing titanium oxide or zinc oxide, which are ultraviolet scattering agents, to be stably blended (mixed) into the oil phase, and also providing excellent sunscreen effects.

Means for Solving the Problem

As a result of carrying out diligent investigations towards solving the above-mentioned problem, the present inventors discovered that a cosmetic having good stability and having a fresh feeling in use while providing excellent sunscreen effects can be obtained by introducing an α-gel structure in an oil-in-water emulsion cosmetic in which an ultraviolet scattering agent having a hydrophobic surface is blended into the oil phase, while also blending a water-soluble alkyl-substituted polysaccharide derivative into the water phase, thereby completing the present invention.

In other words, the present invention provides an oil-in-water emulsion cosmetic characterized by comprising:
(A) an ultraviolet scattering agent having a hydrophobic surface;
(B) a water-soluble alkyl-substituted polysaccharide derivative;
(C) a higher alcohol; and
(D) a non-ionic surfactant.

Effects of the Invention

The oil-in-water emulsion cosmetic of the present invention allows an ultraviolet scattering agent, having a hydrophobic surface, to be stably blended into the oil phase, so that such a cosmetic can provide high ultraviolet protection ability across a wide wavelength range. Furthermore, when applied to the skin, no greasiness or stickiness take place, and a fresh and crisp feeling in use (skin-care sensation) will be attained as if a milky lotion can impart.

MODES FOR CARRYING OUT THE INVENTION

The oil-in-water emulsion cosmetic (hereinafter also referred to simply as "emulsion cosmetic") of the present invention contains an ultraviolet scattering agent (component A) having a hydrophobic surface.

A zinc oxide or titanium oxide powder is preferably used as the substrate for forming the (A) ultraviolet scattering agent having a hydrophobic surface in the emulsion cosmetic of the present invention.

The zinc oxide and the titanium oxide used in the present invention may be of any of ultraviolet scattering agents that can normally be blended into sunscreen cosmetics. For example, a zinc oxide or a titanium oxide in which the average particle size of primary particles is 0.005 μm or larger is preferably used. The average particle size in the present specification refers to an average particle size of primary particles of the ultraviolet scattering agent in the final formulation (if each particle is dispersed alone, such a size is based on the particle per se, and if each particle forms a clustered aggregate thereof, such a size is the size based on the clustered aggregate). This average particle size is preferably in the range 0.01 μm to 10 μm, more preferably 0.02 μm to 1 μm, and most preferably 0.02 μm to 0.1 μm. For example, a pigment-grade ultraviolet scattering agent having an average particle size of 0.1 to 1 μm or comprising fine particles having an average particle size of 0.02 to 0.06 μm is preferred.

In the present invention, an ultraviolet scattering agent having a hydrophobic surface, in which the surface of a substrate such as zinc oxide or titanium oxide has been hydrophobically treated, is used.

Examples of the surface hydrophobic treatment method include silicone treatments such as those using methyl hydrogen polysiloxane, methyl polysiloxane and methyl phenyl polysiloxane; fluorine treatments such as those using perfluoroalkyl phosphate esters and perfluoroalcohols; amino acid treatments such as those using N-acylglutamic acid; lecithin treatments; metal soap treatments such as those using aluminum stearate, calcium stearate and magnesium stearate; fatty acid treatments such as those using palmitic acid, isostearic acid, stearic acid, lauric acid, myristic acid, behenic acid, oleic acid, rosin acid and 12-hydroxystearic acid; alkyl phosphate ester treatments; alkoxysilane treatments such as those using methyltrimethoxysilane, ethyltrimethoxysilane, hexyltrimethoxysilane, octyltrimethoxysilane and octyltriethoxysilane; fluoroalkylsilane treatments such as those using trifluoromethylethyltrimethoxysilane and heptadecafluorodecyltrimethoxysilane; fatty acid ester treatments such as those using dextrin fatty acid esters, cholesterol fatty acid esters, sucrose fatty acid esters and starch fatty acid esters; and silica treatments.

The amount of the (A) ultraviolet scattering agent blended into the emulsion cosmetic of the present invention is 2 to 40% by mass, preferably 3 to 20% by mass and more preferably 5 to 15% by mass. If the blended amount is less than 2% by mass, it is difficult to achieve sufficient ultraviolet protection ability (effect). On the other hand, if more than 40% by mass is blended, the emulsion stability and the ease of use may be reduced.

In addition, if a ratio of a product of (blended amount (% by mass) of the (A) ultraviolet scattering agent) and (average primary particle size (μm) of the (A) ultraviolet scattering agent) with respect to (blended amount (% by mass) of the (B) water-soluble alkyl-substituted polysaccharide derivative) is adjusted so as to have the relationship in the below-indicated expression (1), the stability of the cosmetic is further preferably improved.

Expression (1):

$$((A) \text{UV scattering agent(\% by mass))} \times \text{an average primary particle size}(\mu m))/((B)\text{water-soluble alkyl-substituted polysaccharide derivative(\% by mass))} < 70.$$

The emulsion cosmetic of the present invention comprises a (B) water-soluble alkyl-substituted polysaccharide derivative.

Examples of water-soluble alkyl-substituted polysaccharide derivatives (component B) include hydrophobically modified alkyl cellulose and hydrophobically modified sulfonated polysaccharide derivative sugars. Among these, hydrophobically modified alkyl cellulose is particularly preferred.

As the hydrophobically modified alkyl cellulose, an alkyl cellulose that is hydrophobically modified by means of an alkyl group having 14 to 22 carbon atoms is preferred. More specifically, a compound in which a long-chain alkyl group, which is a hydrophobic group, is introduced to a water-soluble cellulose ether derivative, represented by the following general formula (I), is preferred.

[Chem. 1]

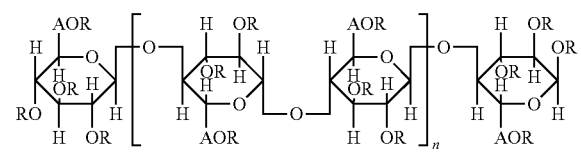

(I)

[In the formula (I), R may be either identical or different, and is one or more groups selected from the group consisting of a hydrogen atom, an alkyl group having 1 to 4 carbon atoms, the group —[CH$_2$CH(CH$_3$)O]$_m$—H (wherein m is an integer from 1 to 5, preferably 1 to 3), the group —CH$_2$CH$_2$OH and the group —CH$_2$CH(OH)CH$_2$OR' (wherein R' is an alkyl group having 14 to 22 carbon atoms). With the proviso that R must mandatorily include at least one group —CH$_2$CH(OH)CH$_2$OR'. Additionally, A represents the group —(CH$_2$)$_q$— (where q is an integer from 1 to 3, preferably 1), and n represents an integer from 100 to 10000, preferably 500 to 5000.]

Generally speaking, the method for producing the hydrophobically modified alkyl cellulose in the aforementioned formula (I) comprises a step of contacting a water-soluble cellulose ether derivative, which is to form the base material, specifically, methyl cellulose (wherein R is a hydrogen atom or a methyl group), ethyl cellulose (wherein R is a hydrogen atom or an ethyl group), propyl cellulose (wherein R is a hydrogen atom or a propyl group), butyl cellulose (wherein R is a hydrogen atom or a butyl group), hydroxypropyl cellulose [wherein R is a hydrogen atom or a hydroxypropyl group (the group —[CH$_2$CH(CH$_3$)O]$_m$—H (wherein m is an integer from 1 to 5, preferably 1 to 3))] or hydroxypropylmethyl cellulose (wherein R is a hydrogen atom, a methyl group or a hydroxypropyl group (same as above)), with a compound for introducing a long-chain alkyl group having 14 to 22 carbon atoms, specifically, the long-chain alkyl glycidyl ether of the below-indicated formula (II) under the presence of an alkali catalyst.

[Chem. 2]

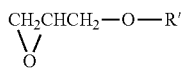
(II)

[R' is an alkyl group having 14 to 22 carbon atoms.]

The amount of the group —CH$_2$CH(OH)CH$_2$OR' introduced to the hydrophobically modified alkyl cellulose of the present invention is preferably approximately 0.1 to 5.0% by mass relative to the hydrophobically modified alkyl cellulose overall. In order to achieve such a content, the compound should be produced by appropriately selecting the molar ratio, reaction time, and type of alkali catalyst when reacting the water-soluble cellulose ester derivative with the long-chain alkylglycidyl ether. The above-mentioned reaction may be followed by a purification process such as neutralization, filtration, washing, drying and sifting of the reactant.

Among the above-mentioned water-soluble cellulose ether derivatives, it is particularly preferable to select hydroxypropyl methylcellulose (as a result thereof, the R in formula (I) becomes one of four types of groups including a hydrogen atom, a methyl group, the group —[CH$_2$CH(CH$_3$)O]$_m$—H and the group —CH$_2$CH(OH)CH$_2$OR', i.e. q in the group A is 1, so the group A becomes a methylene group).

Furthermore, the R' in the long-chain alkyl glycidyl ether in formula (II) is an alkyl group having 14 to 22 carbon atoms, preferably an alkyl group having 14 to 20 carbon atoms, and more preferably a stearyl group (—C$_{18}$H$_{37}$) having 18 carbon atoms. If there are fewer than 14 or no fewer than 23 carbon atoms in the alkyl group R', the emulsion stability of the resulting hydrophobically modified alkyl cellulose can become insufficient.

The weight-average molecular weight of the hydrophobically modified alkyl cellulose is preferably 100,000 to 1,000,000, more preferably 300,000 to 800,000, and even more preferably 550,000 to 750,000.

In the present invention, the use of stearoxy hydroxypropyl cellulose as the hydrophobically modified alkyl cellulose is most preferred, and commercially available products may be used. Examples include Sangelose 90L (label name: hydrophobic hydroxypropyl methylcellulose; manufactured by Daido Chemical Corp.), Natrosol Plus 330cs (manufactured by Ashland Inc.) and Polysurf 67cs (manufactured by Ashland Inc.).

The blended amount of the water-soluble alkyl-substituted polysaccharide derivative (component B) in the emulsion cosmetic of the present invention is 0.01 to 1% by mass, preferably 0.05 to 0.5% by mass, and more preferably 0.1 to 0.3% by mass. If the amount is less than 0.01% by mass, sufficient emulsion stability cannot be obtained, and it is difficult to obtain further increase in the effects even if more than 1% by mass is blended.

(C) Higher Alcohol

The higher alcohol (component C) used in the sunscreen cosmetic of the present invention is not particularly limited as long as it is a higher alcohol having 6 or more carbon atoms that can be used in fields such as cosmetic products, pharmaceutical products and quasi-drug products, and includes saturated linear monohydric alcohols, unsaturated monohydric alcohols and the like.

Examples of saturated linear monohydric alcohols include dodecanol (lauryl alcohol), tridodecanol, tetradodecanol (myristyl alcohol), pentadecanol, hexadecanol (cetyl alcohol), heptadecanol, octadecanol (stearyl alcohol), nonadecanol, icosanol (arachyl alcohol), heneicosanol, docosanol (behenyl alcohol), tricosanol, tetracosanol (carnaubyl alcohol), pentacosanol and hexacosanol (ceryl alcohol).

Examples of unsaturated monohydric alcohols include elaidyl alcohol and the like. In the present invention, saturated linear monohydric alcohols are preferable in terms of stability over time.

As the higher alcohol in the present invention, it is possible to use one or a combination of two or more of the above-mentioned types. In the present invention, it is preferable to use a mixture of two or more aliphatic alcohols, and mixtures of combinations such that the melting point of the mixture is 60° C. or higher are particularly preferred in terms of stability. For example, a combination of stearyl alcohol with behenyl alcohol can be given as a particularly preferable combination.

The blended amount of the higher alcohol (component C) is preferably 0.1 to 10% by mass, more preferably 0.1 to 5% by mass relative to the total mass of the cosmetic. If the blended amount of the (C) higher alcohol is less than 0.1% by mass or more than 10% by mass, sufficient emulsion stability may not be achieved.

(D) Non-Ionic Surfactant

The non-ionic surfactant (component D) used in the oil-in-water emulsion cosmetic of the present invention is not particularly limited. Specific examples include polyethylene glycol fatty acid esters, polyoxyethylene glyceryl fatty acids, polyoxyethylene/methylpolysiloxane copolymers, polyoxyethylene sorbitan fatty acids, polyoxyethylene alkyl ethers, maltitol hydroxy aliphatic alkyl ethers, alkylated polysaccharides, alkylglucosides, sucrose fatty acid esters, polyoxyethylene glyceryl hydrogenated castor oil, polyoxyethylene sorbitan fatty acid esters, polyoxyethylene/polyoxypropylene block copolymers, tetrapolyoxyethylene/tetrapolyoxypropylene-ethylene diamine condensates, polyoxyethylene-beeswax/lanolin derivatives, alkanol amides, polyoxyethylene-propylene glycol fatty acid esters, polyoxyethylene-alkylamines, polyoxyethylene-fatty acid amides, alkylethoxydimethylamine oxide and trioleylphosphoric acid. In the cosmetic of the present invention, hydrophilic non-ionic surfactants having an HLB of 8 or higher, for example, beheneth-20, polysorbate 60 and PEG-40 stearate, can be named as particularly preferable examples. One or more types of non-ionic surfactants may be used.

The blended amount of the non-ionic surfactant (component D) is preferably 0.1 to 20% by mass, more preferably 0.3 to 5% by mass relative to the total mass of the cosmetic. If the blended amount of the (D) non-ionic surfactant is less than 0.1% by mass or more than 20% by mass, sufficient emulsion stability may not be achieved.

(E) Water

The emulsion cosmetic of the present invention is an oil-in-water emulsion containing water (component E) as the external phase.

In the present invention, the aforementioned (C) higher alcohol forms, together with the (D) non-ionic surfactant and the (E) water, an aggregate (also known as an "α-gel") having a lamellar liquid-crystal structure.

(F) Oil Component

The oil component (component F) contained in the internal phase of the sunscreen cosmetic of the present invention contains (f1) an oil-based ultraviolet absorbing agent, and (f2) an oil-based component other than an ultraviolet absorbing agent.

Examples of the oil-based ultraviolet absorbing agent (component f1) include a wide range of high-polarity oil-based ultraviolet absorbing agents that are commonly used in cosmetics. Examples include benzoic acid derivatives, salicylic acid derivatives, cinnamic acid derivatives, dibenzoylmethane derivatives, β,β-diphenylacrylate derivatives, benzophenone derivatives, benzylidene camphor derivatives, phenylbenzoimidazole derivatives, triazine derivatives, phenylbenzotriazole derivatives, anthranil derivatives, imidazoline derivatives, benzalmalonate derivatives and 4,4-diaryl butadiene derivatives. Specific examples and product names will be listed below, but there is no limitation thereto.

Examples of benzoic acid derivatives include ethyl para-aminobenzoate (PABA), ethyl-dihydroxypropyl PABA, ethylhexyl-dimethyl PABA (e.g. "Escalol 507"; ISP), glyceryl PABA, PEG-25-PABA (e.g. "Uvinul P25"; BASF) and hexyl diethylamino hydroxybenzoyl benzoate (e.g. "Uvinul A Plus").

Examples of salicylic acid derivatives include homosalate ("Eusolex HMS"; Rona/EM Industries), ethylhexyl salicylate (e.g. "Neo Heliopan OS"; Haarmann & Reimer), dipropylene glycol salicylate (e.g. "Dipsal"; Scher) and TEA salicylate (e.g. "Neo Heliopan TS"; Haarmann & Reimer).

Examples of cinnamic acid derivatives include octyl methoxycinnamate or ethylhexyl methoxycinnamate (e.g. "Parsol MCX"; Hoffman-La Roche), isopropyl methoxycinnamate, isoamyl methoxycinnamate (e.g. "Neo Heliopan E1000"; Haarmaan & Reimer), cinnoxate, DEA methoxycinnamate, diisopropyl methylcinnamate, glyceryl ethylhexanoate dimethoxycinnamate, and di-(2-ethylhexyl)-4'-methoxybenzalmalonate.

Examples of dibenzoyl methane derivatives include 4-tert-butyl-4'-methoxy dibenzoyl methane (e.g. "Parsol 1789").

Examples of β,β-diphenyl acrylate derivatives include octocrylene (e.g. "Uvinul N539"; BASF).

Examples of benzophenone derivatives include benzophenone-1 (e.g. "Uvinul 400"; BASF), benzophenone-2 (e.g. "Uvinul D50"; BASF), benzophenone-3 or oxybenzone (e.g. "Uvinul M40"; BASF), benzophenone-4 (e.g. "Uvinul MS40"; BASF), benzophenone-5, benzophenone-6 (e.g. "Helisorb 11"; Norquay), benzophenone-8 (e.g. "SpectraSorb UV-24"; American Cyanamid), benzophenone-9 (e.g. "Uvinul DS-49"; BASF) and benzophenone-12.

Examples of benzylidene camphor derivatives include 3-benzylidene camphor (e.g. "Mexoryl SD"; Chimex), 4-methylbenzylidene camphor, benzylidene camphor sulfonic acid (e.g., "Mexoryl SL"; Chimex), camphor benzalkonium methosulfate (e.g. "Mexoryl SO"; Chimex), terephthalylidene dicamphor sulfonic acid (e.g. "Mexoryl SX"; Chimex) and polyacrylamide methylbenzylidene camphor (e.g. "Mexoryl SW"; Chimex).

Examples of phenylbenzoimidazole derivatives include phenylbenzoimidazole sulfonic acid (e.g. "Eusolex 232"; Merck) and disodium phenyldibenzimidazole tetrasulfonate (e.g. "Neo Heliopan AP"; Haarmann & Reimer).

Examples of triazine derivatives include anisotriazine (e.g. "Tinosorb S"; Ciba Specialty Chemicals), ethylhexyl triazone (e.g. "Uvinul T150"; BASF), diethylhexyl butamido triazone (e.g. "Uvasorb HEB"; Sigma 3V), 2,4,6-tris (diisobutyl-4'-aminobenzalmalonate)-s-triazine and 2,4,6-tris[4-(2-ethylhexyloxycarbonyl)anilino]-1,3,5-triazine.

Examples of phenylbenzotriazole derivatives include drometrizole trisiloxane (e.g. "Silatrizole"; Rhodia Chimie) and methylene bis(benzotriazolyl tetramethylbutyl phenol) (e.g. "Tinosorb M" (Ciba Specialty Chemicals)).

Examples of anthranil derivatives include menthyl anthranilate (e.g. "Neo Heliopan MA"; Haarmann & Reimer).

Examples of imidazoline derivatives include ethylhexyl dimethoxybenzylidene dioxoimidazoline propionate.

Examples of benzalmalonate derivatives include polyorganosiloxanes having a benzalmalonate functional group (e.g. Polysilicone-15; "Parsol SLX"; DSM Nutrition Japan).

Examples of 4,4-diarylbutadiene derivatives include 1,1-dicarboxy (2,2'-dimethylpropyl)-4,4-diphenylbutadiene.

The ultraviolet absorbing agent (component f1) may be either just one type or a combination of two or more types. Examples include a combination of octyl methoxycinnamate, octocrylene and oxybenzone, or a combination of octyl methoxycinnamate, octocrylene, polysilicone-15 and 2,4,6-tris[4-(2-ethylhexyloxycarbonyl)anilino]-1,3,5-triazine.

The (f2) oil(-based) component other than the ultraviolet absorbing agent may be any oil component, which is normally blended into a cosmetic, that includes polar oils having a dielectric constant of approximately 5 or higher, and non-polar oils having a dielectric constant less than approximately 5. In the present invention, it is possible to use either or both polar oils and non-polar oils, and to use just one oil component or combine two or more oil components.

Ester oils can be named as representative examples of polar oils. Specific examples of ester oils that are preferred in the present invention include tripropylene glycol dineopentanoate, isononyl isononanoate, isopropyl myristate, cetyl octanoate, octyldodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl 12-hydroxystearate, cetyl ethylhexanoate, ethylene glycol di-2-ethylhexanoate, dipentaerythritol fatty acid ester, N-alkylglycol monoisostearate, neopentyl glycol dicaprate, diisostearyl malate, glycerin di-2-heptylundecanoate, trimethylolpropane tri-2-ethylhexanoate, trimethylolpropane triisostearate, pentaerythrityl tetra-2-ethylhexanoate, triethylhexanoin (glycerin tri-2-ethylhexanoate), glycerin trioctanoate, glycerin triisopalmitate, trimethylolpropane triisostearate, cetyl 2-ethylhexanoate, 2-ethylhexyl palmitate, glycerin trimyristate, glyceride tri-2-heptylundecanoate, castor oil fatty acid methyl ester, oleyl oleate, acetoglyceride, 2-heptylundecyl palmitate, diisobutyl adipate, N-lauroyl-L-glutamate-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate and triethyl citrate.

While the non-polar oil blended in the emulsion cosmetic of the present invention is not particularly limited, it should preferably be selected from the group consisting of volatile or non-volatile silicone oils and hydrocarbon oils.

Specific examples include linear silicone oils such as polydimethylsiloxane, methylphenylpolysiloxane and methyl hydrogen polysiloxane, cyclic silicone oils such as octamethylcyclotetrasiloxane, decamethylcyclopentasiloxane and dodecamethylcyclohexasiloxane, and hydrocarbon oils such as decane, dodecane, isododecane, isohexadecane, liquid paraffin, squalane, squalene and paraffin.

The blended amount of the oil component (component F) in the emulsion cosmetic of the present invention is 5 to 75% by mass, preferably 25 to 50% by mass.

When (G) a liquid higher fatty acid and/or a sugar ester having a carboxyl group in the structure thereof is preferably blended into the emulsion cosmetic of the present invention, the dispersion properties of the ultraviolet scattering agent are improved, and the stability is made even better.

(g1) Liquid Higher Fatty Acid

Examples of the liquid higher fatty acid (component g1) that can be used in the emulsion cosmetic of the present invention include isostearic acid, oleic acid, linoleic acid and linolenic acid. Isostearic acid is particularly preferred.

The blended amount of the liquid higher fatty acid (component g1) is preferably 0.01 to 5% by mass, more preferably 0.02 to 3% by mass, and most preferably 0.05 to 2% by mass, relative to the total mass of the cosmetic. If the blended amount of the liquid higher fatty acid is less than 0.01% by mass or exceeds 5% by mass, the (A) ultraviolet scattering agent may not be evenly and stably dispersed.

(g2) Sugar Ester Having a Carboxyl Group in the Structure Thereof

The sugar ester having a carboxyl group in the structure thereof (component g2) used in the emulsion cosmetic of the present invention forms the internal phase (oil phase) in the oil-in-water emulsion cosmetic, and enables the (A) ultraviolet scattering agent in the oil phase to be evenly dispersed.

Examples of the sugar ester having a carboxyl group in the structure thereof (component g2) include sorbitan sesquiisostearate, dipentaerythritol fatty acid ester, polyoxyethylene sorbitan monooleate and polyoxyethylene sorbitan monostearate. Sorbitan sequiisostearate is particularly preferred.

The blended amount of the sugar ester having a carboxyl group in the structure thereof (component g2) is preferably 0.1 to 5% by mass, more preferably 0.2 to 3% by mass and most preferably 0.3 to 2% by mass, relative to the total mass of the cosmetic. If the blended amount of the sugar ester having a carboxyl group in the structure thereof is less than 0.1% by mass or exceeds 5% by mass, the ultraviolet scattering agent may not be evenly and stably dispersed.

The other arbitrary components, which can normally be blended into conventional cosmetics or quasi-drugs, may be blended into the emulsion cosmetic of the present invention, within a range not impairing the effects of the present invention. The other arbitrary components are not limited, but may, for example, be powder components (other than component A), humectants, aqueous thickeners, dispersing agents, preservatives, fragrances and various medicinal agents.

Examples of powder components include extender pigments such as talc, mica and kaolin, and polymer powders such as polyethylene powder, polymethyl methacrylate powder and nylon powder.

Examples of humectants include polyhydric alcohols such as dynamite glycerol, 1,3-butylene glycol, dipropylene glycol and propylene glycol, and water-soluble polymers such as hyaluronic acid and chondroitin sulfate.

Examples of aqueous thickeners include succinoglycan, (dimethylacrylamide/sodium acryloyldimethyl taurate) crosspolymers, cellulose gum, xanthan gum and (hydroxyethyl acrylate/sodium acryloyldimethyl taurate) copolymers.

The sunscreen cosmetic of the present invention preferably has a lower viscosity, not higher than 12,000 mPa·s, when the viscosity is measured with a B-type viscometer at 30° C. The viscosity of the emulsion cosmetic of the present invention may, for example, be 9,000 mPa·s or lower, or 8,000 mPa·s or lower. By adjusting the viscosity to provide such low level, the feeling in use is made fresh and crisp as if a skin-care milky lotion can make, even while providing high ultraviolet protection ability (effect).

The sunscreen cosmetic of the present invention may be produced in accordance with conventional methods for producing oil-in-water emulsion cosmetics. It may be provided in the form of sunscreen cosmetics in various forms, such as a milky lotion, a liquid or a low-viscous cream.

The emulsion cosmetic of the present invention has the fresh feeling in use that is characteristic of oil-in-water emulsions, and further contains a water-soluble alkyl-substituted polysaccharide derivative, thereby enhancing the fresh feeling. Furthermore, the ultraviolet scattering agent can be stably blended by introducing an α-gel structure, so that excellent ultraviolet protection effects are obtained across a wide wavelength range from the UVA range to the UVB range.

EXAMPLES

Herebelow, the present invention will be explained in further detail by providing specific examples, but the present invention is not limited by these examples in any way. Where not specially noted, the blended amounts are in % by mass relative to the total mass of the composition in which the relevant components are blended.

Oil-in-water emulsion cosmetics were prepared with the formulations shown in Table 1 to Table 3 below. Viscosity of each cosmetic (sample) according to respective example was measured (using B-type viscometer, 30° C.) the day after preparation, and evaluated regarding the following categories (1) to (4) in accordance with the criteria indicated below.

(1) Stability

Evaluation Criteria:

A+: Very stable emulsion was obtained and absolutely no change took place over time.

A: Stable emulsion was obtained, and no separation or aggregation took place over time.

B: Emulsion was obtained, but separation or aggregation of the product took place over time.

C: Emulsion could not be obtained.

(3) Feeling in Use (Dewiness, Ability to Blend into Skin, Non-Stickiness)

Tests of actual use were performed by expert panelists, and the feeling in use was evaluated, from the above-mentioned viewpoints, according to the criteria indicated below.

A: Excellent
B: Somewhat
C: Poor

TABLE 1

| | Ex. 1 | Ex. 2 | Ex. 3 | Ex. 4 | Ex. 5 |
|---|---|---|---|---|---|
| Water | balance to total of 100 | | | | |
| Ethanol | 5 | 5 | 5 | 5 | 5 |
| Glycerin | 6 | 6 | 6 | 6 | 6 |
| 1,3-Butylene glycol | 6 | 6 | 6 | 6 | 6 |
| Xanthan gum | 0.2 | 0.2 | 0.2 | 0.2 | 0.2 |

TABLE 1-continued

|  | Ex. 1 | Ex. 2 | Ex. 3 | Ex. 4 | Ex. 5 |
|---|---|---|---|---|---|
| Hydrophobically modified alkyl cellulose | 0.1 | 0.1 | 0.1 | 0.1 | 0.1 |
| Polyoxyethylene behenyl ether | 1 | 1 | 1 | 1 | 1 |
| PEG/PPG-14/7 dimethyl ether | 2 | 2 | 2 | 2 | 2 |
| Behenyl alcohol | 1 | 1 | 1 | 1 | 1 |
| Stearyl alcohol | 0.2 | 0.2 | 0.2 | 0.2 | 0.2 |
| Caprylyl methicone | 5 | 5 | 5 | 5 | 5 |
| Methyl polysiloxane | 2 | 2 | 2 | 2 | 2 |
| Decamethyltetrasiloxane | 10 | 10 | 10 | 10 | 10 |
| Isostearic acid | 0.1 | 0.1 | 0.05 | 0.2 | — |
| Sorbitan sesquiisostearic | — | — | — | — | 0.2 |
| Polyoxybutylene polyoxypropylene glycol | — | 2 | — | — | — |
| Octyl methoxycinnamate | 3 | 5 | 3 | 3 | 3 |
| Octocrylene | 5 | 5 | 5 | 5 | 5 |
| Oxybenzone | 2 | — | 2 | 2 | 2 |
| Diethylamino hydroxybenzoyl hexyl benzoate | — | 1 | — | — | — |
| Polysilicone-15 | — | 2 | — | — | — |
| 2,4,6-tris[4-(2-ethylhexyloxycarbonyl)anilino]-1,3,5-triazine | — | 2 | — | — | — |
| Hexamethylene diisocyanate/trimethylol hexyllactone crosspolymer | — | — | — | — | — |
| Talc | 6 | 6 | 6 | 6 | 6 |
| Citric acid | s.a. | s.a. | s.a. | s.a. | s.a. |
| Sodium citrate | s.a. | s.a. | s.a. | s.a. | s.a. |
| Edetic acid | s.a. | s.a. | s.a. | s.a. | s.a. |
| Hydrophobically treated zinc oxide (50 nm) | 10 | 10 | 10 | 10 | 10 |
| Value of expression (1) | 5.0 | 5.0 | 5.0 | 5.0 | 5.0 |
| Viscosity (mPa · s/30° C.) | 6000 | 6000 | 7830 | 7100 | 6850 |
| Stability | A+ | A+ | A | A | A |
| Dewiness | A | A | A | A | A |
| Ability to blend into skin | A | A | A | A | A |
| Non-stickiness | A | A | A | A | A |

TABLE 2

|  | Ex. 6 | Ex. 7 | Ex. 8 | Ex. 9 |
|---|---|---|---|---|
| Water | balance to total of 100 | | | |
| Ethanol | 5 | 5 | 5 | 5 |
| Glycerin | 6 | — | — | 3 |
| 1,3-Butylene glycol | 6 | 7 | 7 | 3 |
| Succinoglycan | — | — | — | 0.1 |
| (Dimethylacrylamide/sodium acryloyldimethyl taurate) crosspolymer | — | — | — | 0.2 |
| Xanthan gum | 0.2 | 0.5 | 0.5 | — |
| (Hydroxyethyl acrylate/sodium acryloyldimethyl taurate) copolymer, squalane, polysorbate 60, water, sorbitan isostearate | — | — | — | 0.5 |
| Hydrophobically modified alkyl cellulose | 0.2 | 0.05 | 0.05 | 0.05 |
| Polyoxyethylene hydrogenated castor oil | — | — | — | 1 |
| Lauryl PEG-9 polydimethylsiloxyethyl dimethicone | — | — | — | 0.5 |
| Polyoxyethylene behenyl ether | 1 | 1 | 1 | 0.2 |
| PEG/PPG-14/7 dimethyl ether | 2 | 2 | 2 | 2 |
| Behenyl alcohol | 1 | 1 | 1 | 1 |
| Stearyl alcohol | 0.2 | 0.4 | 0.4 | 0.2 |
| Caprylyl methicone | 5 | 5 | 5 | 5 |
| Methyl polysiloxane | 2 | — | — | — |
| Decamethyltetrasiloxane | 10 | 17 | 17 | 20 |
| Amodimethicone | — | — | — | 1.5 |
| Isostearic acid | 0.1 | 0.1 | 0.1 | 0.3 |
| Polyoxybutylene polyoxypropylene glycol | 2 | 2 | 2 | — |
| Octyl methoxycinnamate | 5 | 10 | 10 | 5 |
| Octocrylene | 5 | — | — | — |
| Bis-ethylhexyloxyphenol methoxyphenyl triazine | 3 | — | — | — |
| Diethylamino hydroxybenzoyl hexyl benzoate | 1 | — | — | — |
| Hexamethylene diisocyanate/trimethylol hexyllactone crosspolymer | — | 3 | 3 | 5 |
| Talc | 6 | 3 | 3 | — |
| Silicic anhydride | 0.2 | — | 0.3 | — |
| Citric acid | s.a. | s.a. | s.a. | s.a. |
| Sodium citrate | s.a. | s.a. | s.a. | s.a. |
| Edetic acid | s.a. | s.a. | s.a. | s.a. |
| Hydrophobically treated zinc oxide (50 nm) | 10 | 10 | 10 | — |
| Hydrophobically treated titanium oxide (200 to 300 nm) | — | — | — | 10 |

TABLE 2-continued

|  | Ex. 6 | Ex. 7 | Ex. 8 | Ex. 9 |
|---|---|---|---|---|
| Value of expression (1) | 2.5 | 10 | 10 | 50-60 |
| Viscosity (mPa·s/30° C.) | 11600 | 3610 | 3900 | 5400 |
| Stability | A+ | A+ | A+ | A |
| Dewiness | A | A | A | A |
| Ability to blend into skin | A | A | A | A |
| Non-stickiness | A | A | A | A |

TABLE 3

|  | Comp. Ex. 1 | Comp. Ex. 2 | Comp. Ex. 3 | Comp. Ex. 4 | Comp. Ex. 5 | Comp. Ex. 6 |
|---|---|---|---|---|---|---|
| Water | balance to total of 100 | | | | | |
| Ethanol | 6 | — | 5 | 5 | 12 | 12 |
| Glycerin | 5 | 5 | 5 | 5 | 2 | 2 |
| 1,3-Butylene glycol | — | 5 | 3 | 5 | 5 | 5 |
| Polyethylene glycol 400 | — | — | — | — | 5 | 5 |
| Trehalose | — | 1 | 1 | 1 | — | — |
| Succinoglycan | 0.1 | — | 0.3 | — | — | — |
| (Dimethylacrylamide/sodium acryloyldimethyl taurate) crosspolymer | 0.5 | — | — | 0.4 | 0.3 | 0.3 |
| Cellulose gum | 0.2 | — | — | — | — | — |
| Xanthan gum | — | 0.1 | 0.1 | 0.2 | — | — |
| Hydrophobically modified alkyl cellulose | — | — | — | 0.1 | 0.2 | 0.5 |
| Polyoxyethylene hydrogenated castor oil | 3 | — | 3 | 1.5 | — | — |
| Polyoxyethylene behenyl ether | 1 | 1 | 1 | — | — | — |
| PEG/PPG-14/7 dimethyl ether | — | 2 | 2 | 2 | — | — |
| Behenyl alcohol | 1 | 1 | 1 | — | — | — |
| Stearyl alcohol | 0.2 | 0.3 | 0.3 | — | — | — |
| Caprylyl methicone | 5 | 5 | — | 3 | 2 | 2 |
| Cetyl 2-ethylhexanoate | — | — | — | — | 1 | 1 |
| Methyl polysiloxane | — | 2 | 2 | 2 | — | — |
| Isododecane | 10 | 7 | 14 | 9 | — | — |
| Isostearic acid | 1 | 1 | — | 1 | — | — |
| Sesquiisostearic acid | 0.5 | 0.5 | — | 0.5 | — | — |
| Polyoxybutylene polyoxypropylene glycol | — | — | — | — | 2 | 2 |
| Octyl methoxycinnamate | 10 | 3 | 3 | 3 | 5 | 5 |
| Octocrylene | — | 5 | 5 | 5 | 5 | 5 |
| Oxybenzone | — | 2 | 2 | 2 | 1 | 1 |
| Bis-ethylhexyloxyphenol methoxyphenyl triazine | 1 | — | — | — | — | — |
| Diethylamino hydroxybenzoyl hexyl benzoate | 1 | — | — | — | — | — |
| Polysilicone-15 | 2 | — | — | — | — | — |
| 2,4,6-tris[4-(2-ethylhexyloxycarbonyl)anilino]-1,3,5-triazine | 1 | — | — | — | — | — |
| Talc | — | 6 | 6 | 6 | — | — |
| Citric acid | s.a. | s.a. | s.a. | s.a. | s.a. | s.a. |
| Sodium citrate | s.a. | s.a. | s.a. | s.a. | s.a. | s.a. |
| Edetic acid | s.a. | s.a. | s.a. | s.a. | s.a. | s.a. |
| Hydrophobically treated zinc oxide (50 nm) | — | 10 | 10 | 10 | 10 | 10 |
| Hydrophobically treated zinc oxide (20 to 30 nm) | 10 | — | — | — | — | — |
| Value of expression (1) | — | — | — | 5.0 | 2.5 | 1.0 |
| Viscosity (mPa·s/30° C.) | 12000 | 4200 | 7000 | 7600 | 17800 | 28000 |
| Stability | A+ | B | A+ | C | B | A+ |
| Dewiness | C | C | C | A | A | A |
| Ability to blend into skin | A | A | A | C | C | C |
| Non-stickiness | A | A | A | A | A | C |

As shown in Table 1 and Table 2, Examples 1 to 9, which contain a higher alcohol (component C) and a non-ionic surfactant (component D) forming an α-gel, as well as water-soluble alkyl-substituted polysaccharide derivative (hydrophobically modified alkyl cellulose: Sangelose 90L, manufactured by Daido Chemical Corp.), despite providing low viscosities of 12000 mPa·s or lower, had been steadily holding the ultraviolet scattering agent (zinc oxide), providing a fresh feeling in use, excellently compatible with skin, and even giving no sticky sensation at all.

In contrast therewith, Comparative Examples 1 to 3, which does not contain a water-soluble alkyl-substituted polysaccharide derivative, failed in giving a fresh sensation and the stability thereof was poor (Comparative Example 2). Additionally, Comparative Example 4, which does not contain a higher alcohol and a non-ionic surfactant forming an α-gel, failed in blending (holding) steadily an ultraviolet scattering agent. Comparative Examples 5 and 6, in which a humectant (polyethylene glycol 400) was added and the water phase was thickened, had a high viscosity, and had poor ability to blend into skin despite improving emulsion stability.

Herebelow, another formulation example for the oil-in-water emulsion cosmetic according to the present invention will be indicated.

The milky lotion for day use of Formulation Example 1 below was evaluated, in the abovementioned evaluation, as having a stability of "A+" and a feeling in use of "A" in all categories.

Formulation Example 1

| Milky Lotion for Day Use | |
|---|---|
| Water | balance to total of 100 |
| Ethanol | 5 |
| Glycerin | 6 |
| Xanthan gum | 0.05 |
| Hydrophobically modified alkyl cellulose | 0.1 |
| Polyoxyethylene behenyl ether | 1 |
| PEG/PPG-14/7 dimethyl ether | 2 |
| Behenyl alcohol | 1.5 |
| Stearyl alcohol | 0.5 |
| Caprylyl methicone | 5 |
| Methyl polysiloxane | 2 |
| Decamethyl tetrasiloxane | 10 |
| Isostearic acid | 0.1 |
| Polyoxybutylene polyoxypropylene glycol | 2 |
| Octyl methoxycinnamate | 5 |
| Bis-ethylhexyloxyphenol methoxyphenyl triazine | 2 |
| Talc | 6 |
| Citric acid | s.a. |
| Sodium citrate | s.a. |
| Edetic acid | s.a. |
| Hydrophobically treated zinc oxide (20 to 30 nm) | 5 |

The invention claimed is:

1. An oil-in-water emulsion cosmetic, comprising:
(A) 2-40% by mass of an ultraviolet scattering agent having a hydrophobic surface;
(B) 0.01-1% by mass of a water-soluble alkyl-substituted polysaccharide derivative;
(C) 0,1-10% by mass of a higher alcohol having 6 or more carbon atoms;
(ii)) 0.1-20% by mass of a non-ionic surfactant, and
(E) water,
wherein the (B) water-soluble alkyl-substituted polysaccharide derivative is a hydrophobically modified alkyl cellulose represented by the following general formula (I):

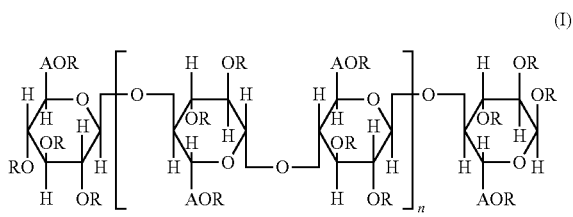

wherein in the formula (I), each R is independently selected from the group consisting of a hydrogen atom, an alkyl group having 1 to 4 carbon atoms, the group —[$CH_2CH(CH_3)O$]$_m$—H (wherein m is an integer from 1 to 5), the group —$CH_2CH_2OH$ and the group —$CH_2CH(OH)CH_2OR'$ (wherein R' is an alkyl group having 14 to 22 carbon atoms), with the requirement that R includes at least one group —$CH_2CH(OH)CH_2OR'$, A represents the group —$(CH_2)_q$— (where q is an integer from 1 to 3), and n represents an integer from 100 to 10000];
wherein an aggregate having a lamellar liquid-crystal structure, which is formed by the (C) higher alcohol, the (D) non-ionic surfactant, and the (E) water, is present in said emulsion cosmetic, and
wherein the viscosity of said emulsion cosmetic is not higher than 12,000 mPa·s as measured using a B-type viscometer at 30° C.

2. The oil-in-water emulsion cosmetic according to claim 1, wherein:
a ratio of a product of (blended amount (% by mass) of the (A) ultraviolet scattering agent) and (average primary particle size (μm) of the (A) ultraviolet scattering agent) with respect to (blended amount (% by mass) of the (B) water-soluble alkyl-substituted polysaccharide derivative) meets a condition indicated by the following expression:

(($A$)UV scattering agent(% by mass)×average primary particle size(μm))/(($B$)water-soluble alkyl-substituted polysaccharide derivative(% by mass))<70.

3. The oil-in-water emulsion cosmetic according to claim 1, further comprising at least one component selected from the group consisting of a liquid higher fatty acid and a sugar ester, wherein said sugar ester is at least one ester selected from the group consisting of sorbitan sesquiisostearate, dipentaerythritol fatty acid ester, polyoxyethylene sorbitan monooleate and polyoxyethylene sorbitan monostearate.

* * * * *